(12) United States Patent
Kazakevich

(10) Patent No.: US 6,692,431 B2
(45) Date of Patent: Feb. 17, 2004

(54) ENDOSCOPIC SYSTEM WITH A SOLID-STATE LIGHT SOURCE

(75) Inventor: Yuri Kazakevich, Andover, MA (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 09/949,430

(22) Filed: Sep. 7, 2001

(65) Prior Publication Data
US 2003/0050534 A1 Mar. 13, 2003

(51) Int. Cl.⁷ .................................................. A61B 1/07
(52) U.S. Cl. .................. 600/178; 600/137; 600/178; 600/182; 362/574; 346/68
(58) Field of Search ................................ 600/112, 137, 600/139–142, 178–182; 362/574; 348/68–70

(56) References Cited

U.S. PATENT DOCUMENTS

| | | |
|---|---|---|
| 4,106,078 A | 8/1978 | Inoue |
| 4,580,551 A * | 4/1986 | Siegmund et al. ........... 600/139 |
| 4,700,693 A * | 10/1987 | Lia et al. .................. 356/241.4 |
| 4,883,333 A | 11/1989 | Yanez |
| 4,969,450 A | 11/1990 | Chinnock et al. |
| 5,036,834 A | 8/1991 | Sugiyama et al. |
| 5,143,435 A | 9/1992 | Kikuchi |
| 5,237,403 A | 8/1993 | Sugimoto et al. |
| 5,491,765 A | 2/1996 | Matsumoto |
| 5,575,757 A | 11/1996 | Kennedy et al. |
| 5,720,706 A * | 2/1998 | Takahashi et al. ............ 348/45 |
| 5,746,494 A | 5/1998 | Koeda et al. |
| 5,797,836 A | 8/1998 | Lucey et al. |
| 5,823,943 A | 10/1998 | Tomioka et al. |
| 5,888,194 A | 3/1999 | Utsumi et al. |
| 5,971,576 A | 10/1999 | Tomioka et al. |
| 6,124,883 A * | 9/2000 | Suzuki et al. .................. 348/68 |
| 6,331,156 B1 * | 12/2001 | Haefele et al. ............. 362/574 |
| 6,371,909 B1 | 4/2002 | Hoeg et al. |

FOREIGN PATENT DOCUMENTS

| | | | |
|---|---|---|---|
| GB | 2339926 | * 2/2000 | .......... G02B/23/26 |
| JP | 10-165362 | * 6/1998 | ............ A61B/1/04 |
| WO | WO 95/15060 | * 6/1995 | ............ H04N/7/18 |
| WO | 96/05693 | 2/1996 | |
| WO | 01/49164 | 7/2001 | |

OTHER PUBLICATIONS

International Search Report; PCT/US 02/27940; Apr. 9, 2003.

* cited by examiner

*Primary Examiner*—John Mulcahy
(74) *Attorney, Agent, or Firm*—Fish & Richardson P.C.

(57) ABSTRACT

An endoscopic system for internal inspection of an object includes an endoscope extending along a longitudinal axis between a distal end to be inserted into the object and a proximal end and an illumination assembly attached to the proximal end of the endoscope. The illumination assembly includes a solid-state light source. The endoscopic system also includes an optical system positioned distally from the solid-state light source to receive and convey light to the distal end.

24 Claims, 10 Drawing Sheets

ENDOSCOPIC SYSTEM WITH A SOLID-STATE LIGHT SOURCE

TECHNICAL FIELD

This invention relates to endoscopic systems with illumination sources.

BACKGROUND

Light sources are used in endoscopy (e.g., medical, industrial). Medical endoscopes are used to inspect regions within the body (e.g., cavities, joints) during surgery (such as laparoscopic/thoracoscopic surgery) through a small puncture. Typically, the endoscope includes a rigid or flexible elongated insertion tube equipped with a set of optical fibers that extend from a proximal handle through the insertion tube to the distal viewing tip of the endoscope. An external light source provides light to the optical fibers via a cable that attaches to the handle (e.g., at a post on the side of the handle) of the endoscope.

SUMMARY

The invention is related to an endoscopic system for internal inspection of an object.

In a general aspect of the invention, the endoscopic system includes an endoscope, an illumination assembly attached to the proximal end of the endoscope and having a solid-state light source, and an optical system positioned distally from the solid-state light source to receive and convey light to the distal end. The endoscope extends along a longitudinal axis between a distal end to be inserted into the object and a proximal end.

Embodiments of this aspect of the invention may include one or more of the following features.

The solid-state light source includes semiconductor light sources (e.g., light emitting diodes (LEDs)).

The solid-state light source includes a hollow shaft having a longitudinal axis and a set of ribs positioned along a periphery of the shaft, each rib having a first side and a second side. The ribs extend along the longitudinal axis of the shaft and are symmetrically spaced around the periphery of the shaft. The first side of each rib has at least one LED and the second side of each rib has at least one LED.

Alternatively, each rib is axially spaced along the longitudinal axis of the shaft. Each rib has at least two LEDs spaced symmetrical on the first side of each rib.

The LEDs are grouped in a trio, each trio has a first LED configured to emit a blue light, a second LED configure to emit a red light, and a third LED configured to emit a green light.

The optical system includes a set of fiber optic elements, each semiconductor light source is configured to emit light to at least one corresponding fiber optic element.

The endoscopic system can further include a camera system proximally positioned to the optical system and a focusing system.

The endoscope is removable and replaceable from the illumination assembly and can further include an eyepiece positioned proximally to the optical system. The endoscope includes a light post, the set of fiber optic elements connecting the solid-state light source to the light post.

The light post is positioned to receive light at an angle to the longitudinal axis.

The endoscopic system further includes a wireless transmitter positioned proximally from the distal end of the endoscope and a battery positioned proximally to the distal end of the endoscope. The endoscope includes an image sensor, for example, positioned proximally to the endoscope.

The endoscope is configured to rotate about the longitudinal axis of the elongated member relative to the stationary imaging sensor.

In another aspect of the invention, the endoscopic system includes an endoscope extending along a longitudinal axis between a distal end to be inserted into the object and a proximal end and a solid-state light source positioned at the endoscope.

Embodiments of this aspect of the invention may include one or more of the following features. The solid-state light source is positioned in the distal end of the endoscope. Alternatively, the solid-state light source is positioned at the proximal end of the endoscope. For example, the solid state light source can be enclosed within a handle portion of the endoscope or as a unit integrally attached to a housing at the proximal end of the endoscope.

Among other advantages, the solid-state light source concentrates light in a small area while providing high luminous emittance. Also, the semiconductor light source more efficiently couples light energy into an optical element (e.g., optic fiber). In general, the solid-state light source is compact and consumes less power. In addition, the solid-state light source responds to changes in applied voltage more quickly than an incandescent lamp or an arc lamp.

The necessity of having a separate light source box and a light guide connected to the scope is eliminated. This greatly improves the user's comfort and ease in maneuvering the device as there is no longer a heavy light guide attached to the scope. A combination of a wireless camera and an endoscope with a built-in solid-state light source will render a completely self-contained wireless endoscope.

DETAILED DESCRIPTION

Figure 1:
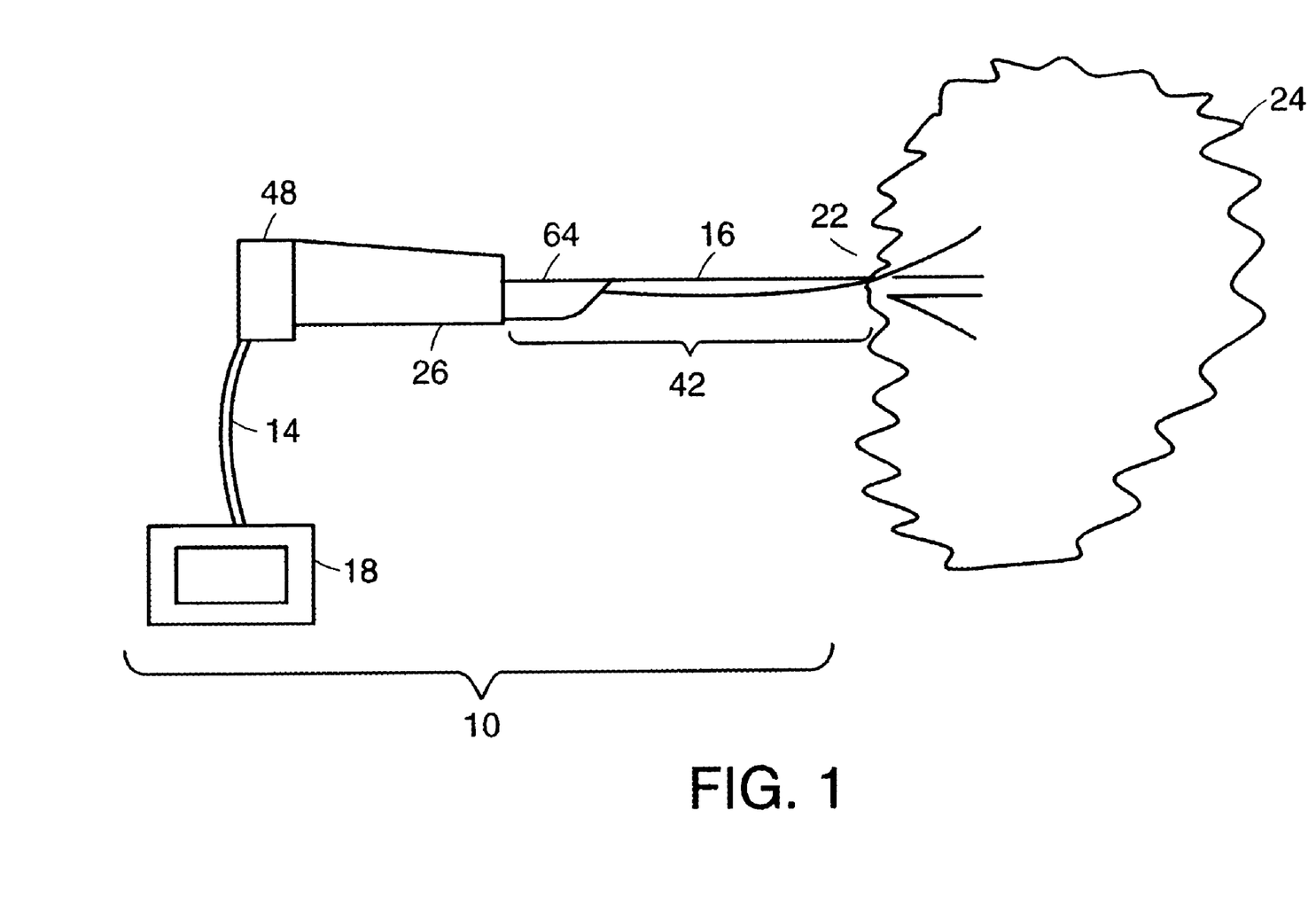
FIG. 1 is a block diagram of an endoscopic system having a solid-state light source attached to an endoscope.

Referring to FIG. 1, an endoscopic system 10 includes an endoscope 42 having a rigid insertion section 16 and a proximal body 64. Endoscopic system 10 also includes an illumination assembly 26 connected to proximal body 64 of endoscope 42. As will be explained in greater detail, illumination assembly 26 includes a solid-state light source assembly 44 (FIG. 2) for generating white light that is conveyed to a working area 24 via insertion section 16. Illumination assembly 26 also encloses a focusing assembly 46 (FIG. 2) used to provide focused images from working area 24 to a video camera assembly 48. Illumination assembly 26 serves as a portion of the endoscopic system 10 used by a surgeon to hold and manipulate endoscope 42 at working area 24. Video camera assembly 48 is connected to illumination assembly 26 and transmits video signals representative of images at working area 24 for display on video monitor 18 thru cable 14.

Figure 2:
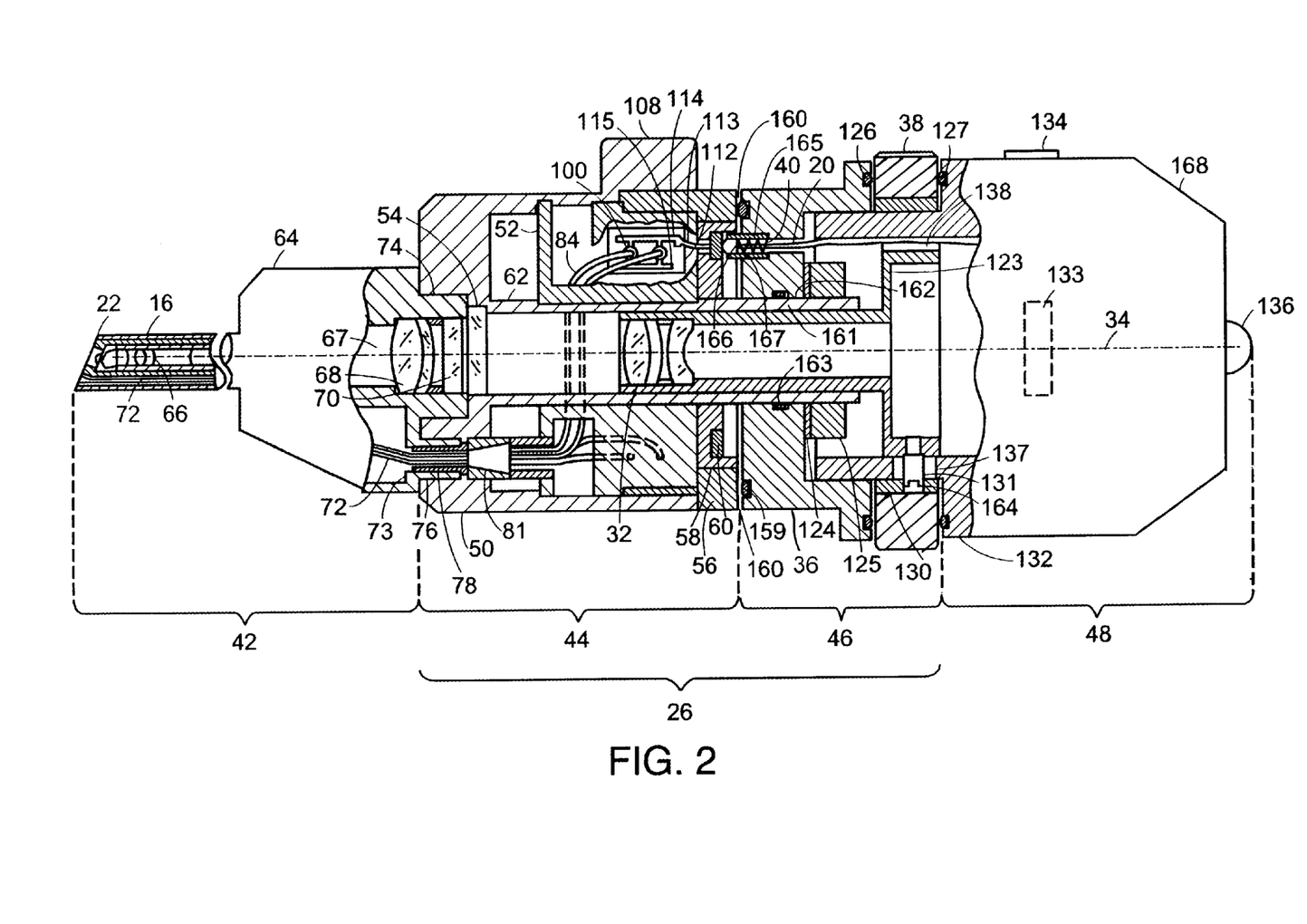
FIG. 2 is a cross-sectional side view of the endoscope, an illumination assembly, and a video camera assembly.

Referring to FIG. 2, solid-state light assembly 44 provides illumination to working area 24 from multiple LEDs 100 through a series of fiber optic connections (e.g. fiber optic bundle 72, fiber optic line 84). The illuminated images from working area 24 are conveyed to camera assembly 48 through an optical path. The optical path extends from distal end 22 through an optical train 66 in endoscope 42 through a set of focusing optics 32 in focusing assembly 46 to video camera assembly 48. Adjusting focusing optics 32 focuses the illuminated images.

Endoscope 42 is an interchangeable component of endoscopic system 10 which can be interchanged with endoscopes of other configurations. In this embodiment, insertion section 16 is rigid and has a direction of view offset from a longitudinal axis 34 of the insertion section. As stated above, endoscope 42 contains fixed optics 68 which can include a single lens or a group of lenses situated after a field stop. Endoscope 42 also includes a proximal window 70 hermetically sealed with a channel 67 to prevent the introduction of contaminants from the environment including the remaining portions of endoscopic system 10 (e.g., solid-state light source assembly 44).

A fiber optic bundle 72 conveys light extends through endoscope 42 and conveys light from solid-state light source assembly 44 to distal end 22 of the endoscope. At the interface of solid-state light source 44, fiber optic bundle 72 is epoxied into a bushing 78, thereby creating a hermetic seal. In turn, bushing 78 is fixed to proximal body 64 that is also hermetically sealed.

Optics train 66 includes fixed optics 68 and proximal window 70 positioned near solid-state light source assembly 44. Likewise, solid-state light source assembly 44 includes a front window 47 and a light coupling element 81 both of which are hermetically sealed to a housing 50. Thus, endoscope 42 and solid-state light source assembly 44 are independently hermetically sealed, so that other endoscopes may be removably attached to solid-state light source assembly 44 (e.g., flexible endoscopes).

Solid-state light assembly 44 includes a light source/fiber optic assembly 52 positioned within housing 50 having a hollow shaft 62 aligned with longitudinal axis 34.

Figure 3A:
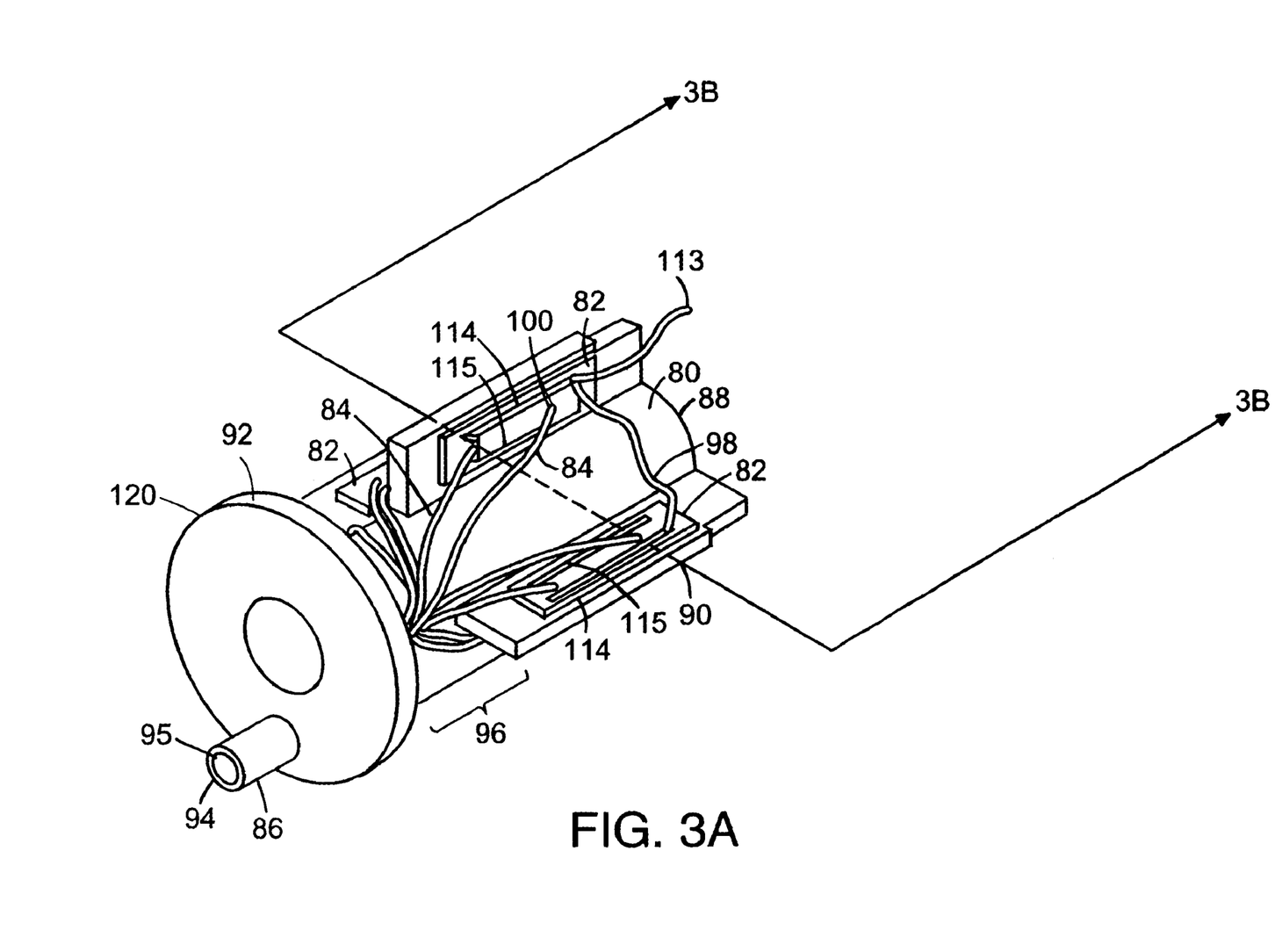
FIG. 3A is a perspective view of a light source/fiber subassembly.
Figure 3B:
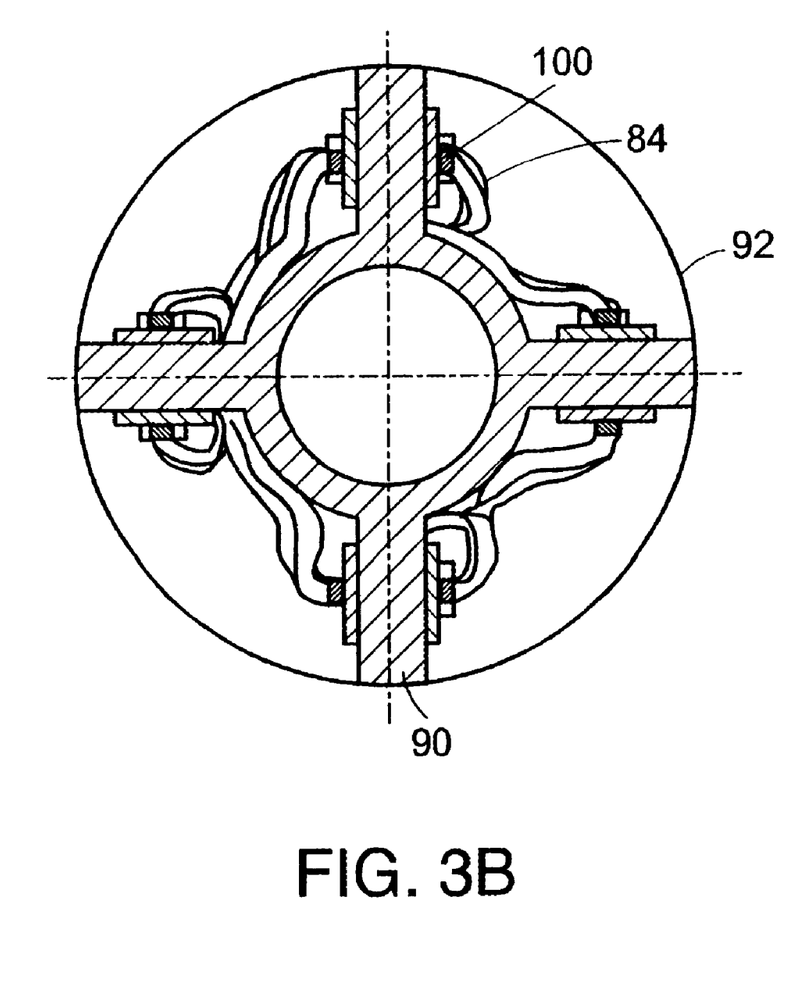
FIG. 3B is an end view of the solid-state light source/fiber subassembly taken along the line 3B—3B.

Referring to FIGS. 3A and 3B, light source/fiber optic subassembly 52 includes a metal frame 80, light source assemblies 82, fiber optic lines 84 and a fiber output fitting 86. Frame 80 includes a hollow shaft 88 with axial ribs 90 and a flange 92. In this embodiment, there are four axial ribs 90 symmetrically arranged along the circumference of hollow shaft 88. Each rib 90 extends the length of hollow shaft 88. Each side of rib 90 has a mounting face for placing light source assemblies 82 so that two light assemblies are mounted per rib.

Within each light source assembly 82 are light emitting diodes (LEDs) 100. Light emitted by each LED 100 is coupled into a corresponding fiber line 84. From each LED 100, corresponding fiber optic lines 84 are all brought together into a common bundle 94 at a distal end 120 of light source/fiber subassembly 52 where the common bundle is received and bonded into fiber output fitting 86. A distal end 95 of common bundle 94 is fine polished in order to create an interface for conveying light into fiber optic bundle 72 located within endoscope 42. As explained below, electric power is provided to LEDs 100 by an electrical connection through a rotational joint 160. The electrical connection includes an insulated wire 20 connected to a power source (not shown) in video camera assembly 48. The electrical connection also includes a wire lead 113 connected to light source/fiber subassembly 52.

An axial space 96 between ribs 90 and flange 92 allows for fiber optic lines 84 coming from different ribs to wrap around the distal part of shaft 88 in order to connect with end fitting 86. A light coupling element 81 is placed at polished distal end of bundle 94. Thus, when light source/fiber subassembly 52 is placed within endoscope 42, light coupling element 81 may interface the polished proximal end of fiber optic bundle 72. Therefore, emitted light from solid-state light source assembly 44 can pass through insertion section 16 to working area 24.

As light source/fiber subassembly 52 is inserted into housing 50, the inside diameter of the hollow shaft 80 of the subassembly slides over the outer diameter of hollow shaft 62. The end of light coupling element 81 is brought into contact with the proximal face of fiber optic bundle 72. Light source/fiber subassembly 52 is secured to housing 50 by attaching rear flange 56 to the open proximal end of the housing 50 by threads. An insulating ring 58, made of an electrically insulating material (e.g., ceramic, plastic), is securely attached to rear flange 56 (e.g., by press fitting, bonding or other fastening method). A contact ring 60, made of a high electrical conductor (e.g., copper), is embedded into the insulating ring 58. Insulated wire lead 113 has one end soldered to the contact ring 60 at one end and an opposite end connected to a positive bus 114 of one of the light source assemblies 82. Each of the light source assemblies 82 includes positive bus 114 which are all interconnected by wires 98. Each of the light source assemblies includes a negative buses 115, each connected to the metal frame 80 which serves as a common ground.

In this embodiment, LEDs 100 are square, approximately 1 mm per side. LEDs 100 emit a blue light. A phosphor layer (not shown) is applied between the LED emitting surface and the entrance face of fiber lines 84. When the blue light passes through the phosphor layer, the blue light excites the phosphor layer causing it to fluoresce green and red light. The green light, red light and blue light together form white light. In other embodiments, LEDs 100 emit ultraviolet light. In still other embodiments, the phosphor layer can be located anywhere along an illumination path of the light (e.g., at an interface of light coupling element 81 and fiber bundle 72 or at distal end 22 of endoscope 42). LEDs 100 suitable for use in this embodiment of solid-state source assembly 44 can be obtained from Lumileds Lighting of San Jose, Calif. Loose fibers, suitable for this embodiment, can be obtained by Schott-Fostec, LLC of Auburn, N.Y.

Referring back to FIG. 2, focusing assembly 46 includes a front portion 36, a focusing ring 38, a contact pin assembly 40, a retainer nut 125, a washer 124, and a lens cell 123 with a focusing lens 32, a focusing sleeve 130, and a lens body 132. Retainer nut 125 is secured to hollow shaft 62 of housing 50 by threads. Low friction washer 124 is placed between nut 125 and front portion 36. Front portion 36 includes a seal 159, e.g., a low drag rubber-like seal. Seal 159 may be in the shape of an O-ring or an X-shaped Quad ring. As nut 125 is threaded onto shaft 62, the nut holds together the solid-state light source assembly 44 and front portion 36 of the focusing assembly 46. The distal end of the front portion 36 abuts the proximal end of rear flange 56 thereby defining rotational joint 160. A lubricant (e.g., high vacuum grease available from Dow Corning Corporation) is applied to seal 159 to ensure its proper functioning.

Solid-state light source housing 50 has a ridge 108 for convenient rotation. In operation, when the user applies a tangential force to ridge 108, the entire solid-state light source assembly 44 rotates relative to front portion 36 of focusing assembly 46. Retaining nut 125 and washer 124 also rotate with solid-state light source assembly 46. An axial alignment between solid-state light source assembly 44 and focusing assembly 46 is maintained by closely providing a tolerance to an interior bearing surface 161 of the front portion 36 and an exterior bearing surface 162 of hollow shaft 62.

Preferably, front portion 36 and shaft 62 are made from different materials, any combination of which produces low friction. The torque required for rotation is determined by frictional forces between the seal 159 and rear flange 56, between interior bearing surfaces 161 and exterior bearing surface 162, and between washer 124 and contacting it surfaces of the nut 125 and front portion 36. The suitable amount of torque is set by applying a proper pressure when nut 125 is threaded over shaft 62. When a specified amount of torque is reached, nut 125 is locked in place using known methods (e.g., with retaining compounds available from Loktite Corp. applied to the threads). An additional O-ring (or multiple O-rings) 163 may be provided for the torque adjustment and additional seal.

With endoscope 42 locked to solid-state light source assembly 44, rotational joint 160 allows for rotation of endoscope 42 around axis 34. Focusing sleeve 130 is surrounded by focusing ring 38 and secured to it by threads, for example. Lens body 132 is attached to front portion 36 preferably by threads. The proximal part of the lens body 132 may act as a front flange of the video camera assembly 48. The distal end of focusing ring 38 abuts the proximal end of the front portion 36 in a sealed relationship. Similarly, the proximal end of focusing ring 38 abuts the distal end of the lens body 132 in a sealed relationship. The dynamic seals 126 and 127 are constructed similarly to the seal 159. Lens cell 123 carries focusing lenses 32 for projecting the image onto the surface of the image pickup device 133.

A cam screw 131 secures lens body 132, the focusing sleeve 130, and the lens cell 123 together. Focusing sleeve 130 includes a helical through slot 164 whose axial length corresponds to the required range of lens cell axial movement for proper focusing. Helical slot 164 receives the upper part of the head of cam screw 131. Lens body 132 includes an axial slot 137 that receives the lower part of the head of cam screw 131. The length of slot 137 also corresponds to the focusing range of lens cell 123. As focusing ring 38 rotates, focusing sleeve 130 being securely attached to the ring also rotates. The head of cam screw 131 rides inside helical slot 164 and inside axial slot 137. Axial component of the helix causes back-and-forth movements of cam screw 131 depending on the direction of rotation of the focusing ring 38. Axial slot 137 prevents rotation of cam screw 131 ensuring only axial motion. As cam screw 131 is securely attached to the lens cell 138, the lens cell 138 will also move axially within limits of the axial length of helical slot 64 and the length of slot 137.

Front portion 36 also includes contact pin assembly 40 which includes a sleeve 165 made out of an electrically insulating material. Contact pin assembly 40 is securely attached to front portion 36 so the contact pin assembly is situated opposite to the contact ring 60 of the solid-state light source assembly 44. A small compression spring 167 is secured inside sleeve 165 (e.g., flared in) so that the compression spring exerts a force onto a conductive pin 166 bringing the pin into a firm contact with contact ring 60. Insulated wire lead 20 is soldered to proximal end of pin 166 and follows through a slot 138 made in lens cell 123 into video camera assembly 48 where the wire lead is connected to the appropriate circuitry for providing the proper voltage level to light sources 100.

Video camera assembly 48 includes an image pickup device 133 (e.g. CCD or CMOS sensor), a housing 168, and an electric cable 136. In operation, the camera head normally is not rotated and is held so that image pickup 133 is maintained in the right-side-up position. By maintaining the right-side-up position regardless of the rotation of the endoscope, the proper orientation of the image is always attained. Normally, camera heads have a protruding feature 134, (e.g. buttons, ridges, etc.) on their top sides giving the user a tactile feeling of the right side up position. Electric cable 136 connects the camera head to a camera control unit (not shown) containing a power supply, a camera motherboard and various auxiliary circuitry for imaging. In other embodiments, video camera assembly 48 contains a battery and all the circuitry necessary to transmit video images to video monitor 18.

In other embodiments, light coupling element 81 may be either omitted altogether or the coupling element may be a part of endoscope 42 by being built into fitting 78. In other embodiments, light coupling element 81 may be attached securely to fitting 86. Light coupling element 81 may be a solid or fiber-optic cone which matches the Numerical Aperture (NA) of bundle 94 and fiber optic bundle 72. In other embodiments, a mixing rod with a square or hexagonal cross-section is used to provide uniform white when using multiple colored LEDs as a light source.

Figure 4A:
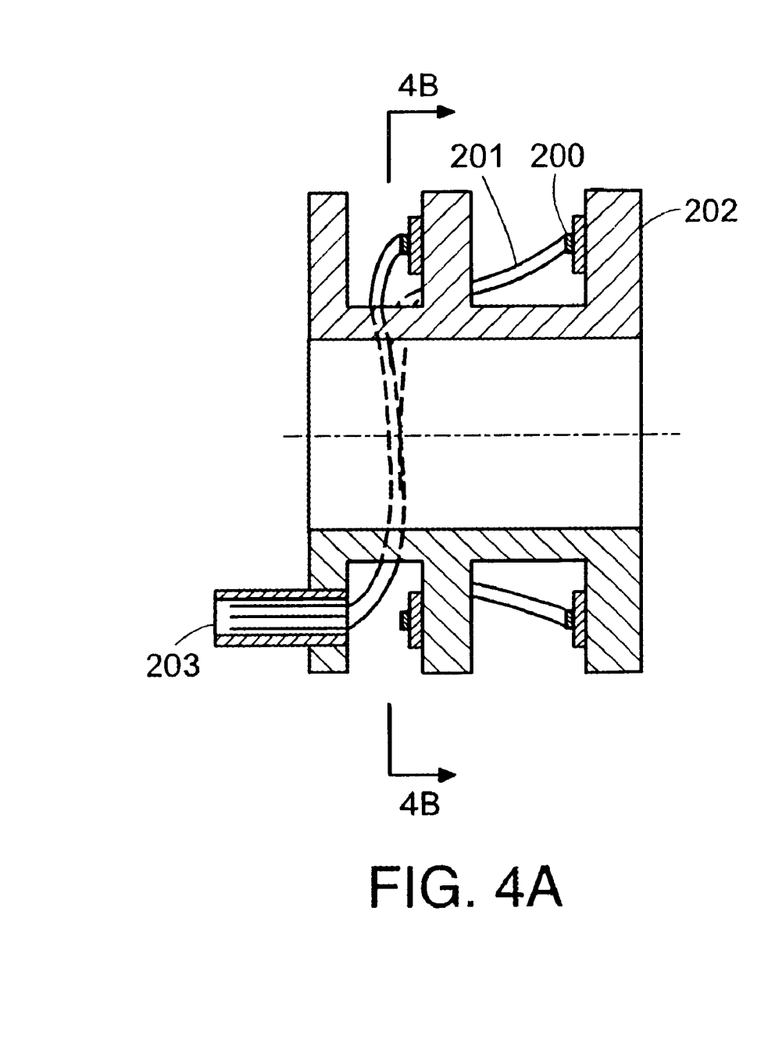
FIG. 4A is a cross-sectional view of another embodiment of the light source/fiber subassembly having ribs axially spaced.
Figure 4B:
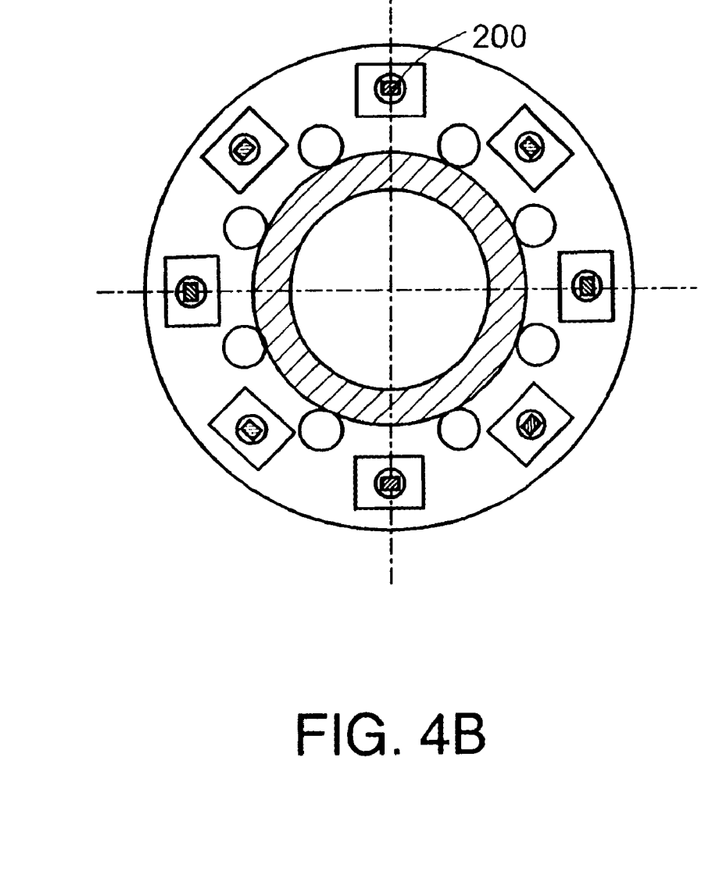
FIG. 4B is an end view taken along lines 4B—4B of FIG. 4A.

Referring to FIGS. 4A and 4B, in other embodiments, there are a number of configurations of the light source/fiber subassembly that are possible. In one embodiment, ribs 202 can be arranged radially so that light sources 200 are situated in a ring fashion on each radial rib. Openings 203 are provided in the distal ribs for the passage of the fiber lines 201 from the proximally located light sources.

In the preferred embodiment (FIG. 2) there is only one contact ring and one pin assembly for the positive voltage transfer. This is sufficient, if the negative buses of the light sources are grounded to the metal frame, because the frame connects to the camera housing common ground through the housing of the solid-state light source assembly and the lens cell. Yet, in many embodiments, a separate ground or negative electric potential would be required for the negative buses because of electrical design considerations. In these embodiments, the contact ring may be split into two concentric mutually insulated rings so that two pins will be used for the voltage transfer.

Also, in the preferred embodiment, the arrangement of having the contact ring and the pin assembly has a potential drawback of having limited reliability in the spring-loaded electrical contact and a possibility of electrical shorts if the seal 159 fails. In addition, there is a limited reliability in the spring-loaded electrical contact.

Figure 5A:
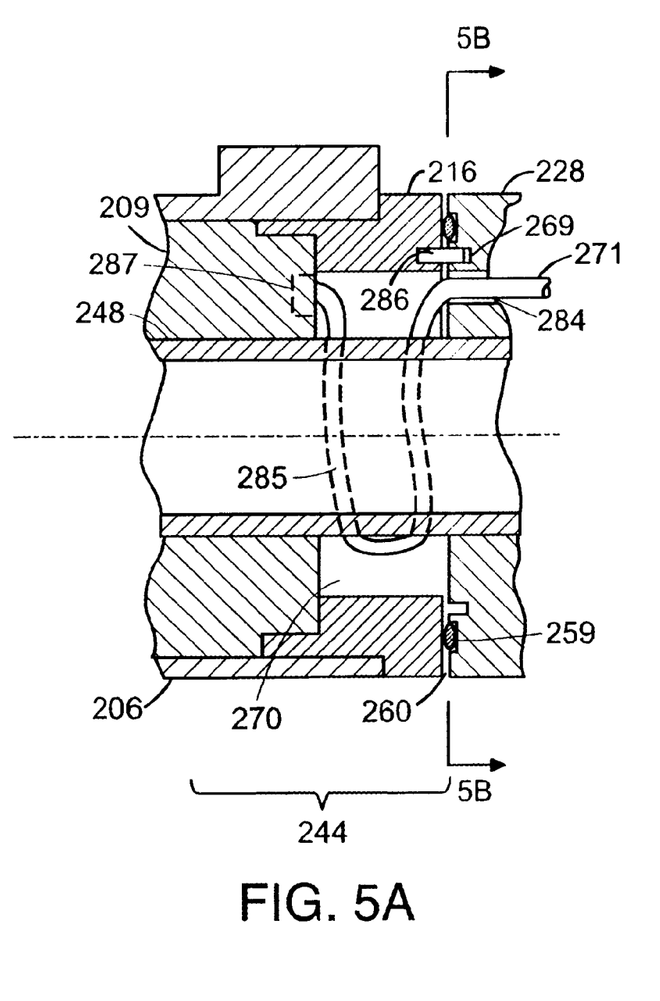
FIG. 5A is a cross-sectional view of another embodiment of the solid-state light source assembly having additional space for fiber optic lines.
Figure 5B:
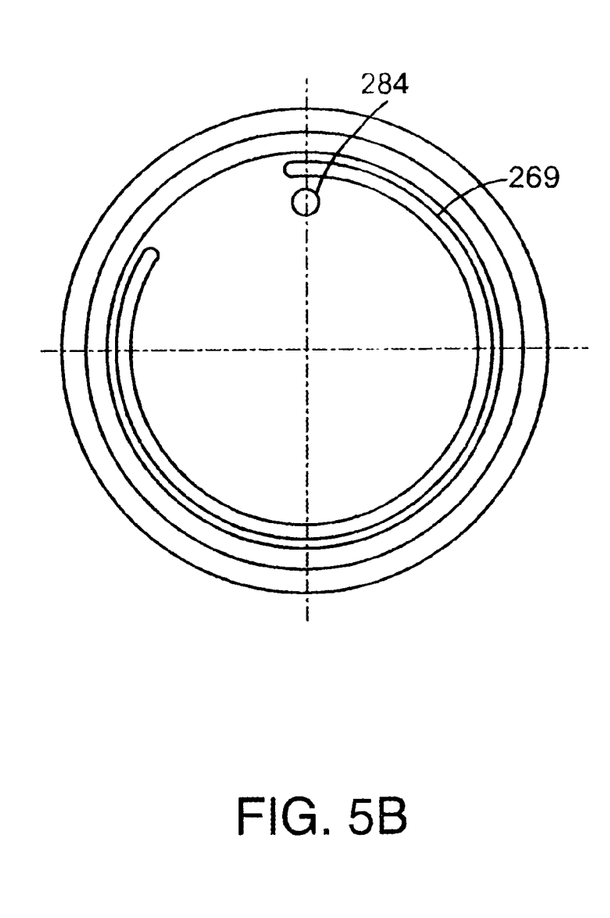
FIG. 5B is an end view taken along lines 5B—5B of FIG. 5A.

Referring to FIGS. 5A and 5B, another embodiment eliminates the insulating ring and the contact ring so that a rear flange 216 becomes one piece. In this configuration, rear flange 216 is constructed so that a gap 270 sufficiently wide is created between the lens body 228 and a light source frame 209. A flexible cable 271 is fixed at the end of opening 284 in lens body 228 and then a sufficient slack 285 is created. A distal end of cable 271 is connected to a connector 287 situated on light source frame 209. From connector 287 the appropriate leads are distributed between the light sources mounted on frame 209. Cable 271 can carry as many leads as needed and may be hardwired (soldered) or connected by pins at both light source and camera ends thus eliminating a sliding electrical contact. As solid-state light assembly 244 rotates, the slack 285 gets taken out. Rear flange 216 is attached to a fixed pin 286 which is received by a circumferential groove 269 made in the lens body 228. Groove 269 subtending a sufficiently large angle, e.g., 320–330°, both ends of groove 269 define two stops to limit the rotation at rotational joint 260 due to finite length of cable 271. In this embodiment, there is no continuous rotation at joint 260, but there is enough rotation to utilize the directional properties of the endoscope and at the same time maintain the correct orientation of the image. This embodiment allows one to use as many leads as necessary to be carried within cable 271. This is especially important if multiple single color LEDs are used for white light generation. Different current levels (and therefore different voltages) may be applied to different color LEDs for optimal color temperature of the resulting white light. Thus, multiple leads will be required to power different light sources.

In other embodiments, the endoscope is integral to the solid-state light source assembly. In this arrangement, fiber optic lines connected to light sources continue directly into the endoscope. This configuration eliminates interfaces at light coupler thereby increasing the light efficiency.

In still other embodiments, the focusing lens and the fixed lens may be designed in various configurations including having additional fixed lens groups securely attached to the camera housing or to any other parts of the camera head.

In another embodiment, the video camera assembly includes not just the camera head, but also rather a self-contained camera which also includes a battery and a wireless transmitter to transmit the video signal to the TV receiver. In this arrangement, the endoscopic system is a completely self-contained wireless system.

Figure 6:
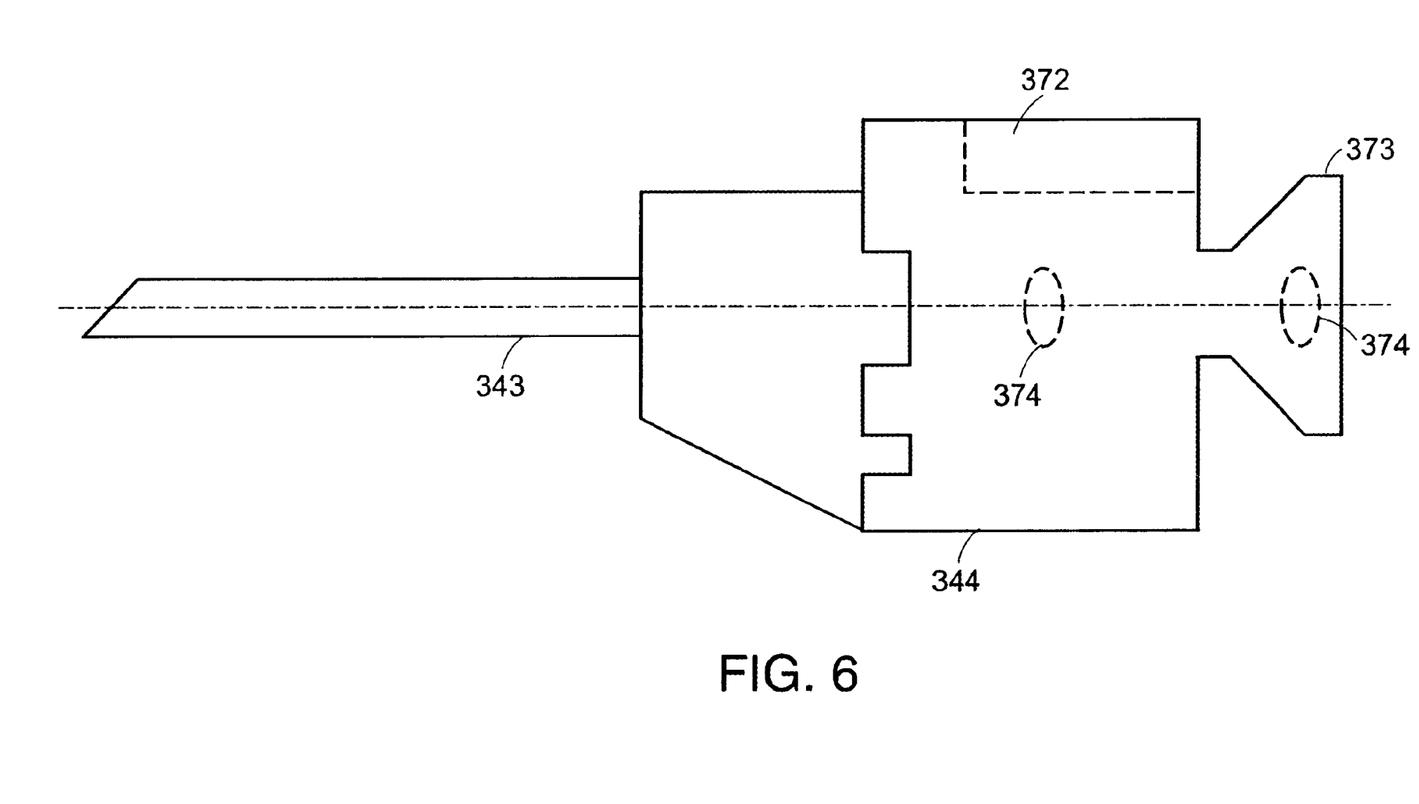
FIG. 6 is cross-sectional view of the endoscope with an eyepiece.

Referring to FIG. 6, all embodiments described thus far included a projection of the endoscope image onto the camera and observing the image on the monitor or with other electronic means, e.g. head mounted displays. However, in many cases direct visualization through the endoscope is sufficient for the task (e.g., quick diagnosis, insertion of anaesthetic tube, industrial applications, etc). The rotational joint is no longer required since the entire system may be rotated without changing the image orientation. An endoscope 343 is removably attached to a solid-state light source assembly 344 designed similarly to the previous embodiments. Solid-state light source assembly 344 includes a battery compartment 372 having a battery to power the light sources (not shown). Solid-state light source assembly 344 connects to an eyepiece 373. The user looks into the eyepiece 373 and visually observes the image. An optical system 374 provides for virtual image formation located at about 250 mm distally from eyepiece 373 suitable for visual observation.

Figure 7:
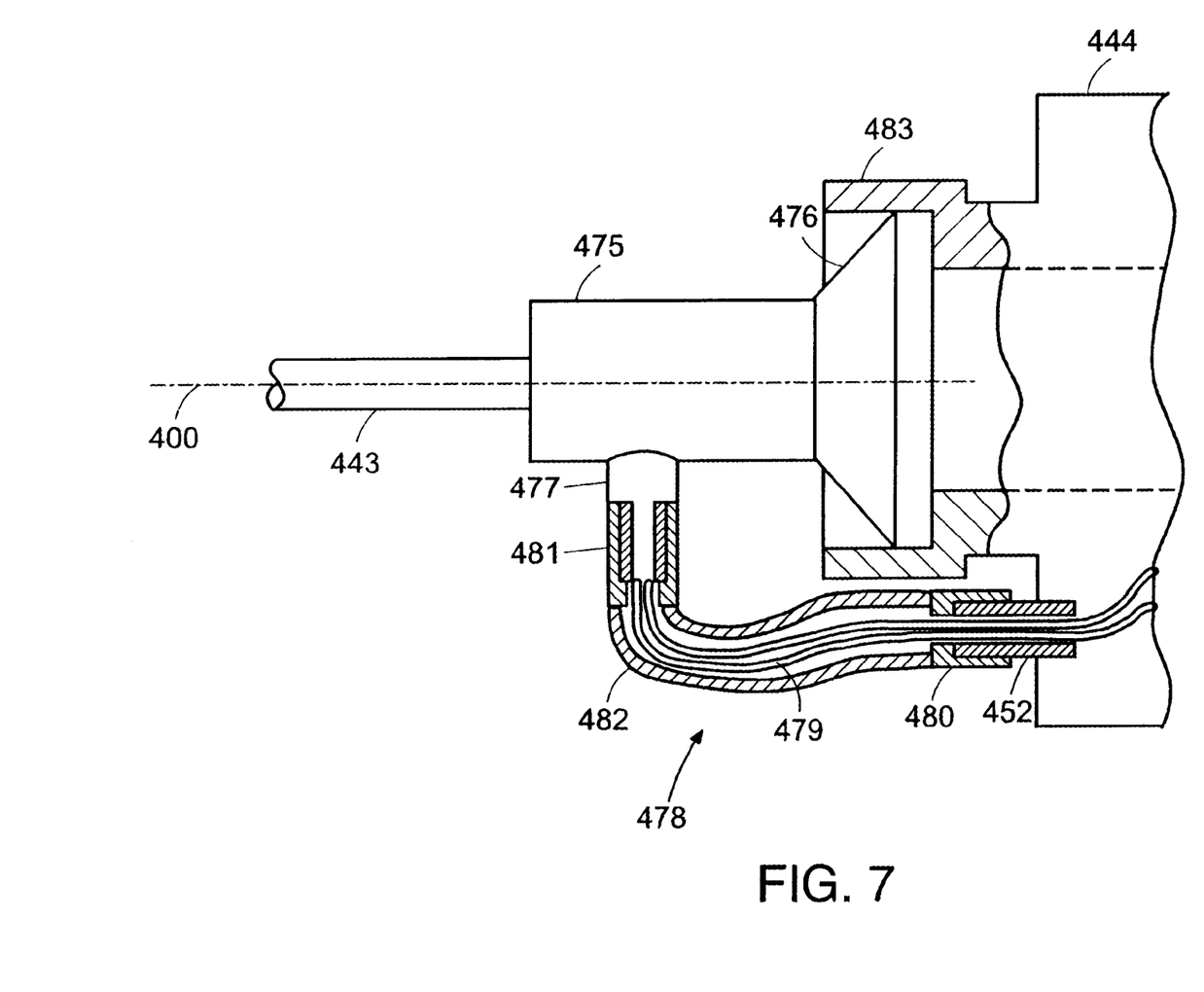
FIG. 7 is a cross-sectional view of another embodiment of the endoscope and the solid-sate light source assembly with an exterior light post fitting.

Referring to FIG. 7, in still other embodiments, a rigid endoscope has a housing 475 with a light post fitting 477 directed at about 90° angle to a longitudinal axis 400 of the endoscope. The endoscope has a standardized eyepiece 476 situated proximally to the body 475. This embodiment can be easy to configure so as to retrofit the existing population of endoscopes. Solid-state light source assembly 444 is arranged so that it has a distal part 483 which receives a standard eyepiece 476 and locks it into place by a locking mechanism (not shown). Fiber fitting 452 is made external to the main body of the solid-state light source 444. A short piece of light cable 478 connects the endoscope light post 477 and the illuminator end fitting 452. The light cable 478, having a fiber bundle 479 and a protective jacket 482, includes female fittings 480 and 481 connected to illuminator end fitting 452 and endoscope light post 477 respectively. In other embodiments, the solid-state light source is small enough to be attached directly to the endoscope (e.g., connected to the light post or built into the proximal body of the endoscope).

Figure 8:
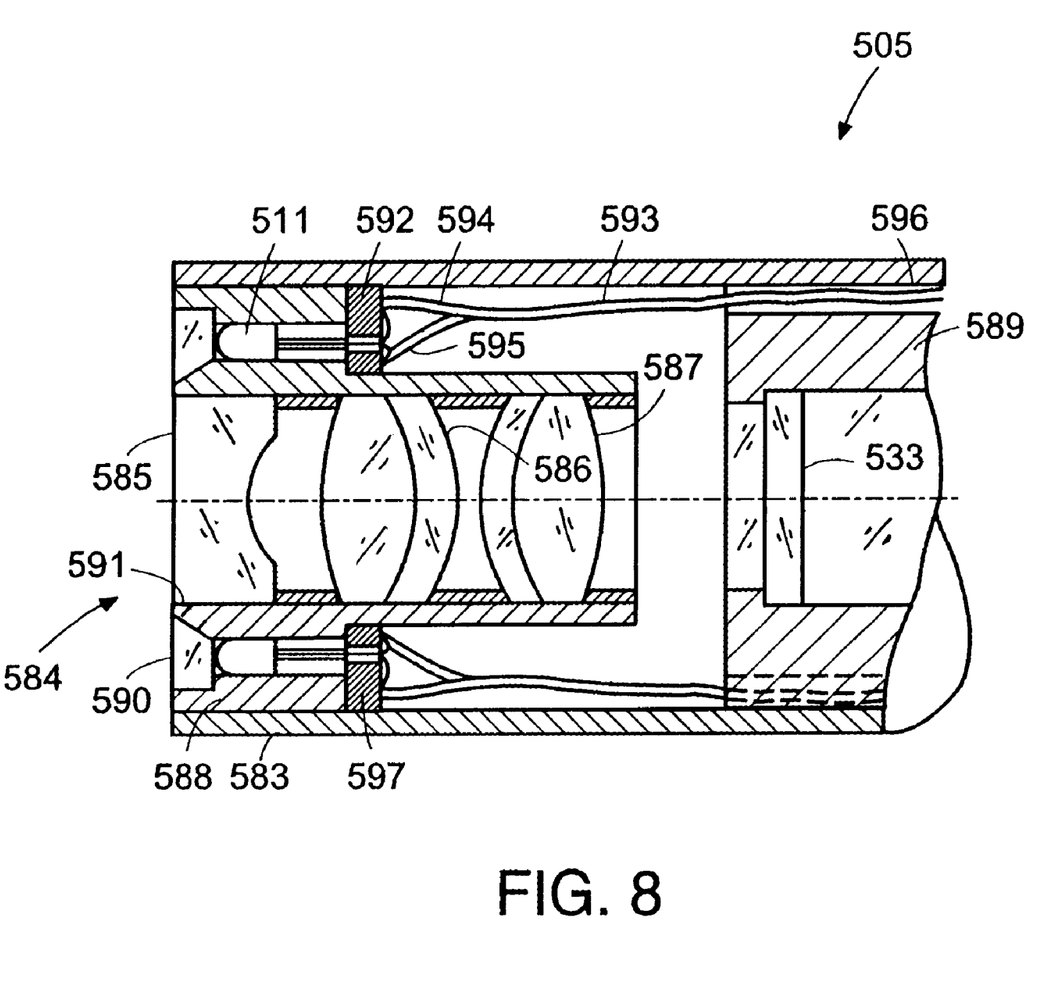
FIG. 8 is a cross-sectional view of an embodiment of a solid-state light source located in a distal end of the endoscope.

Referring to FIG. 8, solid-state light sources 511 (e.g. white LEDs) are placed in a ring-like fashion directly at the distal end of the insertion section 505 of the endoscope. In an electronic endoscope configuration, the image sensor 533 is located at the distal end of the insertion portion. However, similar designs will also apply to the endoscopes with proximal location of the image (e.g., rod-lens endoscopes, fiberscopes). This embodiment is best suited for relatively large diameter endoscopes, for instance, 10 mm diameter endoscopes which are standard in laparoscopy. These embodiments have high-resolution color image sensors such as CCD or CMOS devices are available in small sizes as small as ⅓" format package (3.6 mm). Using small imaging devices and small LED packages makes it possible to situate a ring of LEDs at the distal end of a 10 mm endoscope around an objective lens. The endoscope includes an outer tube 583, a distal housing 588 and an image sensor housing 589. Distal housing 588 houses an objective lens 584. Objective lens includes a front lens 585, a middle lens 586 and a back lens 587. Front lens 585 usually in the shape of a negative lens for the field of view expansion also serves as a front window maintaining the external seal. Alternatively, a separate flat window may be arranged in front of the objective to maintain the seal. The housing 588 at its periphery also contains a ring of LEDs 511. A transparent ring 90 made of optical glass or optical grade sapphire is placed as a seal in front of LED ring to protect the LEDs from harsh surgical or industrial environment. A partition 591 between ring 590 and the front lens 585 of objective lens 584 prevents detrimental back reflections from the front surface of the ring 590 back into the objective 584. A fiberglass printed circuit board 592 is attached to the proximal end of the housing 588. Board 592 has openings 597 to receive positive and negative LED leads that are passed through the openings and soldered to a positive and to a negative bus (not shown) respectively on the proximal side of the board 592. A cable 593 containing at least a positive lead 594 and a negative lead 595 which extends from the proximal portion of the endoscope and powers the LEDs 511. A slot 596 is made in the image sensor housing 589 for the passage of cable 593.

Figure 9:
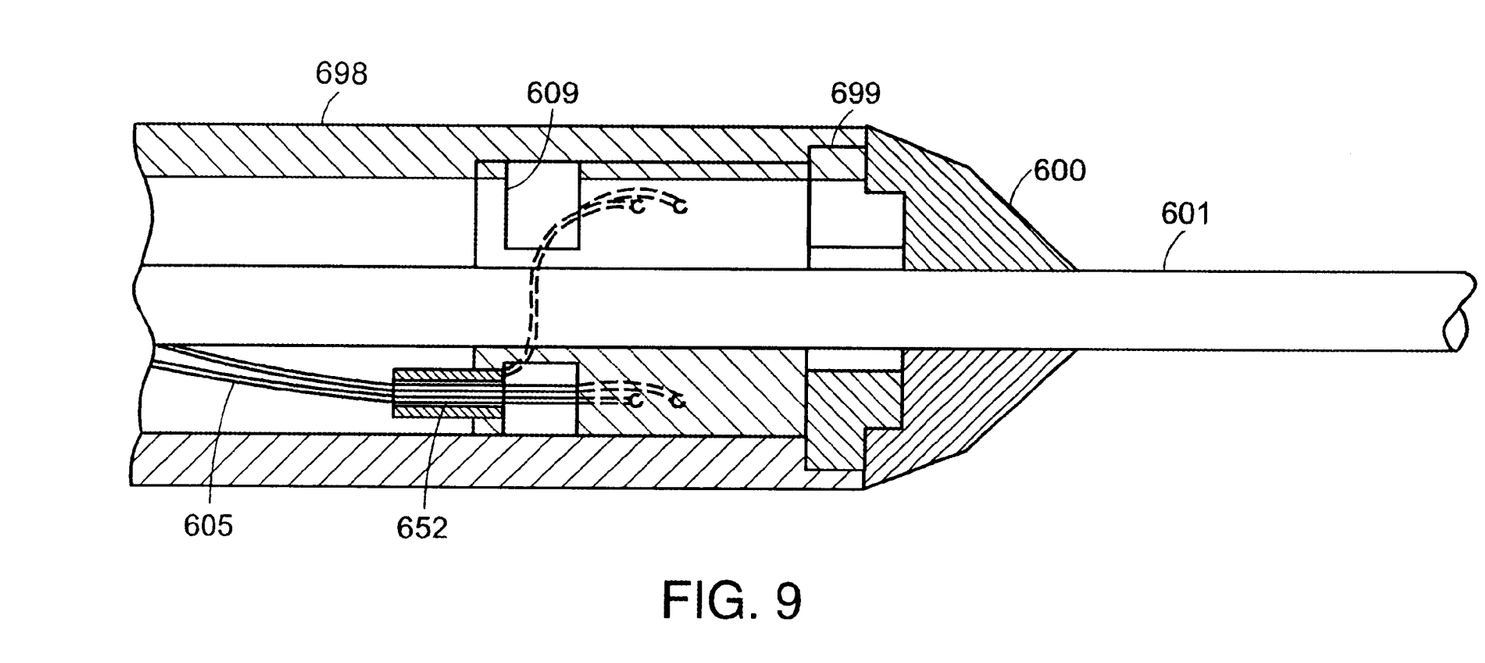
FIG. 9 is a cross-sectional view of an embodiment of a solid-state light source in an electronic endoscope having a distal imager.

Referring to FIG. 9, in other embodiments, electronic endoscopes, having an image sensor distally placed, can be incorporated to have a light source/fiber subassembly 609 in a handle 698. In addition, handle 698 can house a focusing mechanism and a rotation mechanism for correct image orientation. In this configuration, a retainer 699 secures light source/fiber subassembly 609 from the proximal side. The cable molding 600 is attached to retainer 699. Cable molding 600 receives the electric cable 601 which is passed through the opening in light source/fiber subassembly 609 to the distal side. The fiber optic bundle 605 coming from the end fitting 652 extends to the distal end of the endoscope. Alternatively, a fiber-to-fiber or a fiber-to-light coupler joint may be created at the distal end face of fitting 652. In other embodiments, a battery and wireless transmitter may be incorporated into the handle 698 eliminating cable 601 making a wireless electronic endoscope containing no external light or electrical cables protruding from the handle.

Details relating to the semiconductor light sources (e.g., both LED or laser) and the manner in which they are coupled to fiber optical elements are described in U.S. patent application No. 09/944,495, Solid-State Light Source, in the name of Yuri Kazakevich, filed on Aug. 31, 2001 and incorporated herein by reference.

U.S. Pat. Nos. 4,969,450, 5,797,836, and 5,575,757 are also incorporated herein by reference.

Still other embodiments are written within the scope of the claims.

What is claimed is:

1. An endoscopic system for internal inspection of an object comprising:
   an endoscope extending along a longitudinal axis between a distal end to be inserted into the object and a proximal end;
   an illumination assembly attached to the proximal end of the endoscope, the illumination assembly including a solid-state light source, the solid-state light source includes a plurality of semiconductor light sources; and
   an optical system positioned distally from the solid-state light source, the optical system receiving and conveying light to the distal end, the optical system includes a set of fiber optic elements, each semiconductor light source is configured to emit light to one corresponding fiber optic element;
   wherein the solid-state light source includes a hollow shaft having a longitudinal axis and a set of ribs positioned along a periphery of the shaft, each rib having a first side and a second side, wherein the first side of each rib has at least one LED.

2. The endoscopic system of claim 1 wherein the plurality of semiconductor light sources include light emitting diodes (LEDs).

3. The endoscopic system of claim 1 wherein the solid-state light source includes a hollow shaft having a longitudinal axis and a set of ribs positioned along a periphery of the shaft, each rib having a first side and a second side, wherein the first side of each rib has at least one LED.

4. The endoscopic system of claim 1 wherein the ribs extend along the longitudinal axis of the shaft and are symmetrically spaced around the periphery of the shaft.

5. The endoscopic system of claim 4 wherein the second side of each rib has at least one LED.

6. The endoscopic system of claim 1 wherein each rib is axially spaced along the longitudinal axis of the shaft.

7. The endoscopic system of claim 6 wherein each rib has at least two LEDs spaced symmetrical on the first side of each rib.

8. The endoscopic system of claim 2 wherein the LEDs are grouped in a trio, each trio has a first LED configured to emit a blue light, a second LED configure to emit a red light, and a third LED configured to emit a green light.

9. The endoscopic system of claim 1, further comprising:
   a camera system proximally positioned to the optical system; and
   a focusing system.

10. The endoscopic system of claim 1 wherein the endoscope is removable and replaceable from the illumination assembly.

11. The endoscopic system of claim 1, further comprising an eyepiece positioned proximally to the optical system.

12. The endoscopic system of claim 1 wherein the endoscope includes a light post, the set of fiber optic elements connect the solid-state light source to the light post.

13. The endoscopic system of claim 12 wherein the endoscope includes an eyepiece.

14. The endoscopic system of claim 13 wherein the light post is positioned to receive light at an angle to the longitudinal axis.

15. The endoscopic system of claim 1, further comprising a wireless transmitter positioned proximally from the distal end of the endoscope and a battery positioned proximally to the distal end of the endoscope.

16. The endoscopic system of claim 1, wherein the endoscope includes an image sensor.

17. The endoscopic system of claim 1 further comprising an imaging sensor positioned proximally to the endoscope.

18. The endoscopic system of claim 17 wherein the endoscope is configured to rotate about the longitudinal axis of the elongated member relative to the stationary imaging sensor.

19. The endoscopic system of claim 1 wherein each fiber optic element comprises a fiber optic line.

20. The endoscopic system of claim 1 wherein each fiber optic element comprises a bundle of fiber optic lines.

21. An endoscopic system for internal inspection of an object comprising:
   an endoscope extending along a longitudinal axis between a distal end to be inserted into the object and a proximal end;
   an illumination assembly attached to the proximal end of the endoscope, the illumination assembly including a solid-state light source, the solid-state light source includes a plurality of semiconductor light sources;
   an optical system positioned distally from the solid-state light source, the optical system receiving and conveying light to the distal end, the optical system includes a set of fiber optic elements extending from the semiconductor light sources at the proximal end to the distal end, each semiconductor light source is configured to emit light to one corresponding fiber optic element; and
   a focusing assembly enclosed by the illumination assembly;
   wherein the solid-state light source rotates relative to the focusing assembly.

22. The endoscopic system of claim 21, further comprising:
   an image pickup device;
   wherein the image pickup device maintains a right-side-up position independent of the rotation of the endoscope.

23. The endoscopic system of claim 21 wherein each fiber optic element comprises a fiber optic line.

24. The endoscopic system of claim 21 wherein each fiber optic element comprises a bundle of fiber optic lines.

* * * * *